United States Patent [19]
Wu et al.

[11] Patent Number: 5,338,198
[45] Date of Patent: Aug. 16, 1994

[54] DENTAL MODELING SIMULATOR

[75] Inventors: Chuang-Jy Wu; Christopher L. B. Lavelle, both of Winnipeg, Canada

[73] Assignee: DACIM Laboratory Inc., Winnipeg, Canada

[21] Appl. No.: 155,134

[22] Filed: Nov. 22, 1993

[51] Int. Cl.⁵ .................................................. A61C 11/00
[52] U.S. Cl. .................................................. 433/213
[58] Field of Search .................. 433/229, 223, 24, 214, 433/213, 49

[56] References Cited

U.S. PATENT DOCUMENTS

| | | | |
|---|---|---|---|
| 4,611,288 | 9/1986 | Duret et al. | 433/213 |
| 4,742,464 | 5/1988 | Duret et al. | 433/213 |
| 4,837,732 | 6/1989 | Brandestini et al. | 433/223 |
| 4,964,770 | 10/1990 | Steinbichler et al. | 433/223 |

Primary Examiner—Cary E. O'Connor
Attorney, Agent, or Firm—Adrian D. Battison; Stanley G. Ade; Murray E. Thrift

[57] ABSTRACT

A three-dimensional model of the teeth of a patient is prepared by taking molded impressions of the mandibular and maxillar teeth, placing separately the impressions on a support table define an X-Y plane and detecting the Z distance from a probe by directing a beam of laser light onto the impression and calculating from the pattern of reflected light a centre of the light falling on an area array. The scanning in the X-Y plane is effected continuously and is limited by datum points defining a dental arch. The impression is then tilted and the process repeated and information correlated to provide the three-dimensional model. A partial impression is then taken of both mandibular and maxillar teeth in comparison with datum points to provide information concerning the bite (occlusal) positions of the teeth. This information is then compared with the full impression to simulate using the three-dimensional models movement of the jaw from an open position to the bite (occlusal) position.

15 Claims, 2 Drawing Sheets

DENTAL MODELING SIMULATOR

This invention relates to a method for generating a three-dimensional model of the teeth and dental arch of a patient.

BACKGROUND OF THE INVENTION

Whereas in the past, material advances and improved professional manpower training largely determined improvements in the delivery of dental care, now the progressively sophisticated service demands of the public require the introduction of new technologies. To this end, an innovative technique has been developed to improve the quality and efficiency of dental diagnosis, treatment planning and evaluation, in addition to patient communication. In this technique, conventional dental impressions are digitized by a computer-controlled laser scanner. Subsequently these data are transformed by customized computer graphics software, so that the derived three-dimensional electronic models of the teeth and dental arches can be viewed on a computer terminal from any perspective or magnification. Additional software has been developed so that these models can be modified interactively to simulate the effects of treatment prior to actual commencement on a patient. In addition, these models can be readily transmitted to others for advice and/or treatment planning approval, stored on a computer disk for future reference, and integrated with other computer-derived diagnostic data (e.g. digital radiographic or periodontal assessments) thereby facilitating the development of 'expert' systems.

Traditional hydrocolloid casts of the maxillary or mandibular dental arches are ubiquitous to many forms of dental service, due to difficulties in intraoral diagnosis, treatment planning and evaluation. Derived from alginate, silicone or rubber-base impressions, the main applications of study casts are summarized below.

(1). Orthodontics
  (a) Diagnosis,
    (i). dental arch evaluations, including relative tooth alignment and orientation
    (ii). functional occlusal analyses between maxillary and mandibular dentition's, including analysis of wear facets and attrition
    (iii). evaluations of maxillary and mandibular skeletal base relationships
  (b) Treatment planning
    (i). timing of orthodontic treatment
    (ii). decision analysis between orthodontic and/or orthognathic surgical cases
    (iii). orthodontic appliance design
  (c) Treatment progress evaluation
  (d) Treatment case records (2). Prosthetic dentistry
  (a) Diagnosis, including the evaluation of wear and attrition facets
  (b) Treatment planning
    (i). Fixed or removable appliance selection
    (ii). Pre-prosthetic treatment for remaining natural teeth
    (iii). Pretreatment orthodontic tooth realignment
  (c) Appliance design
    (i). Abutment tooth selection
    (ii). Identification of potential rest seat and clasp locations
    (iii). Clasp design and abutment tooth location
    (iv). Pontic design
  (d) Appliance evaluation
  (e) Treatment case records (3). Restorative dentistry
  (a) Treatment planning
    (i). Complex cavity design
    (ii). Restorative material selection
  (b) Treatment case records (4). Pedodontic dentistry
  (a) Diagnosis
  (b) Treatment planning
  (c) Treatment case records (5). Periodontics
  (a) Diagnosis
  (b) Treatment planning
  (b) Treatment case records (6). Patient communication
  (a) Status of present dentition and treatment needs
  (b) Treatment options
  (c) Treatment progress
  (d) Treatment case records (7). Third Party communication
  (a) Pre-authorization insurance company assessment
  (b) Medico-legal documentation.

Yet reliance on study casts has hampered significant improvements to dental service quality and cost efficiency. For instance, visual appraisals of their morphologic form primarily hinge on the biased experience of the observer, whereas the alternatives of ruler, protractor or grid measurements are too restrictive to offer significant improvements to their evaluation. Whereas study cast evaluations are necessary to compensate for difficulties with in situ appraisals of the teeth and dental arches, only a fraction of their component data can be delineated by existing evaluative techniques. Dental diagnosis, treatment planning and evaluation therefore remains largely subjective, and this restricts their objective appraisals required for significant improvements in service quality assurance and cost containment. The primary deficiency of study cast evaluations stems from difficulties in their measurement.

Other deficiencies arise from difficulties in their storage and retrieval due to their physical bulk. Traditional study casts are also static and cannot be readily manipulated, which restricts their applications when evaluating potential treatment options and their presentation to patients. For example, cutting and repositioning teeth on a cast is conventionally used to simulate potential orthodontic realignment options, whereas trial wax-ups on a study cast are often components of complex restorative treatment planning, including abutment tooth selection and pontic design. In cases requiring complex occlusal rehabilitation, spot grinding or other forms of adjustment are often simulated first on study casts prior to commencing treatment on an actual patient. But all techniques involving traditional study casts are relatively crude, subjective and time-consuming, primarily due to difficulties in their precise measurement.

The complex morphologic forms of teeth and dental arches are difficult to measure with any degree of precision. Nevertheless, many techniques have been developed to measure individual or groups of teeth very accurately as a component of CAD/CAM technology applied to dentistry.

Well established in the aerospace, automotive and large manufacturing industries, computer aided manufacturing and computer aided design (CAD/CAM) have significant potential for improved quality and cost efficiency when applied to dentistry. Unfortunately the lack of accurate measurement techniques restricts their application to small complicated biological bodies such as a tooth. Since the accuracy requirements for dental diagnosis, treatment planning and evaluation are similar to precision manufacturing standards, data acquisition is the principal deficiency of current CAD/CAM dental applications. The five measurement techniques reported for CAD/CAM dental applications thus far include the following:

i. Laser probes using structured light principle,
ii. Photogrammetric methods,
iii. Laser range measuring probes with X-Y-Z tables,
iv. Scanning laser range probes,
v. Traditional mechanical coordinate measuring machines.

The CEREC System which has been developed by Brains-Brandestini Instruments of Zollikan, Switzerland (Moermann and Brandestini 1986) and is currently marketed by Siemens Dental Division, FRG (Siemens 1989) and Dr. F. Duret (1988) are both employing a specially designed hand-held probe to measure the three dimensional coordinates of a prepared tooth. The measurement probe design embraces the structured light principle. But in order to eliminate possible image artifacts from dark garnishes on the tooth's surface, saliva, debris etc., a talc and titanium oxide powder mixture combined with a wetting agent must be applied to the area to be measured. Methods to control powder thickness and the resultant masking effect on the fine cavity preparation details have yet to be reported. Due to difficulties in data acquisition and processing from the in situ use of a hand-held optical probe, a modification is using a mechanical arm to hold the probe and a partial study cast of the prepared tooth is actually measured.

The Photogrammetric principle to measure the profile of a prepared tooth cavity is a component of the proposed system developed at the University of Minnesota (Rekow 1987). A pair of stereo images are recorded on the standard film using a modified 35 mm camera with a single-rod lens attached to a laryngopharyngoscope. Major difficulties of this system include saliva and other image contaminants and the automation of tooth profile measurements from stereo images.

The commercial coordinate measuring machine (CMM) has been proposed and a very few examples have been manufactured and used in research establishments. This uses a laser range probe for non contact measurement of a cast model of the teeth of the patient. It has data acquisition rate of only a few points per minutes and more than 12 hours is required to measure a complete cast. An optical CMM (Yamamoto, 1988) with data sampling speed of 25 ms (i.e. 40 data points per sec.) has been reported with measurement accuracy in the range of 100 mm. Approximately 1 hour is required to measure an impression. These devices are therefore of little practical value.

The scanning laser probe described by Rioux (1984) has very high data acquisition rate but is unfortunately very expensive. This has not been proposed for dental modeling but only for industrial operations. This device uses a highly complex moving mirror arrangement to effect the scanning and this leads to the very high cost which makes it completely impractical for the present requirements.

Using traditional coordinate measuring machine or a miniature mechanical arm to capture data from stone dies has been proposed by many researchers (Rekow, 1992). Major disadvantages of a mechanical probe include slow data acquisition speed and limited measurement resolution. Surfaces which have radii of curvature or depression less than the mechanical probe tip radius cannot be detected. With probe tip diameters less than 0.5 mm, their mechanical integrity difficult to maintain, in addition to their potential for surface damage.

As all reported measurement systems suffer from serious deficiencies, none can be considered a viable clinical instrument. Capital costs (laser scanning probe), difficulty in usage (mechanical probe), inaccuracy (optical probe and mechanical probe) or speed (mechanical CMM) limit their routine application for diagnosis, treatment planning or evaluation.

There remains therefore a high requirement for a dental modeling system in view of the following major advantages:

(1). Prior treatment planning simulation
 (a). Simulation of major and minor orthodontic tooth movement facilitates objective appliance design and subsequent evaluation of treatment progress
 (b). Simulation of occlusal rehabilitation with/or without simultaneous orthodontic or prosthodontic treatment would facilitate discrimination between organic and functional occlusal disharmonies and enhance quality assurance in treatment planning
 (c). Simulation of cosmetic, restorative or prosthodontic treatment would enhance the potential for quality assurance of the adjacent hard and soft tissues
 (d). Simulation of potential orthodontic and/or periodontal relapse prior to treatment would provide quality checks in appliance design (2). Communication
 (a). Electronic storage of detailed dental arch measurements would facilitate instantaneous model referral for advice and consultation (Third Party, specialist etc.)
 (b). Dental arch three-dimensional simulations would provide excellent professional patient communication media to explain potential treatment options and their rationale for selection (3). Overhead cost reduction
 (a). As detailed dental arch dimensions can be stored on an office computer, the latter's increased utilization will facilitate service cost containment—The planned system for laser scanning and model simulations will be designed to utilize a standard dental office computer system
 (b). Enhanced quality assurance prior to treatment will reduce the potential for relapse and/or failure
 (c). By elimination the need for model storage, electronic dental arch data storage will facilitate record retrieval and archiving efficiency.

SUMMARY OF THE INVENTION

It is one object of the present invention to provide a method for generating a three-dimensional model of the teeth and dental arch of a patient.

According to the invention therefore there is provided a method of generating for manipulation a three-dimensional model of the teeth and dental arch of a patient comprising taking a molded impression of the teeth, placing the impression on a support table defining an X-Y plane, directing a beam of laser light onto the impression at a point of impact, relatively translating the beam of light and the impression in the X-Y plane so as to scan the impression with the beam to provide a plurality of points of impact each having a predetermined location in the X-Y plane, determining the distances of the points of impact of the beam with the impression in the Z direction by detecting a pattern of light reflected from the point, and generating the digital image by correlating the locations and the distances.

One embodiment of the invention will now be described in conjunction with the accompanying drawings, in which:

DETAILED DESCRIPTION

Figure 1:
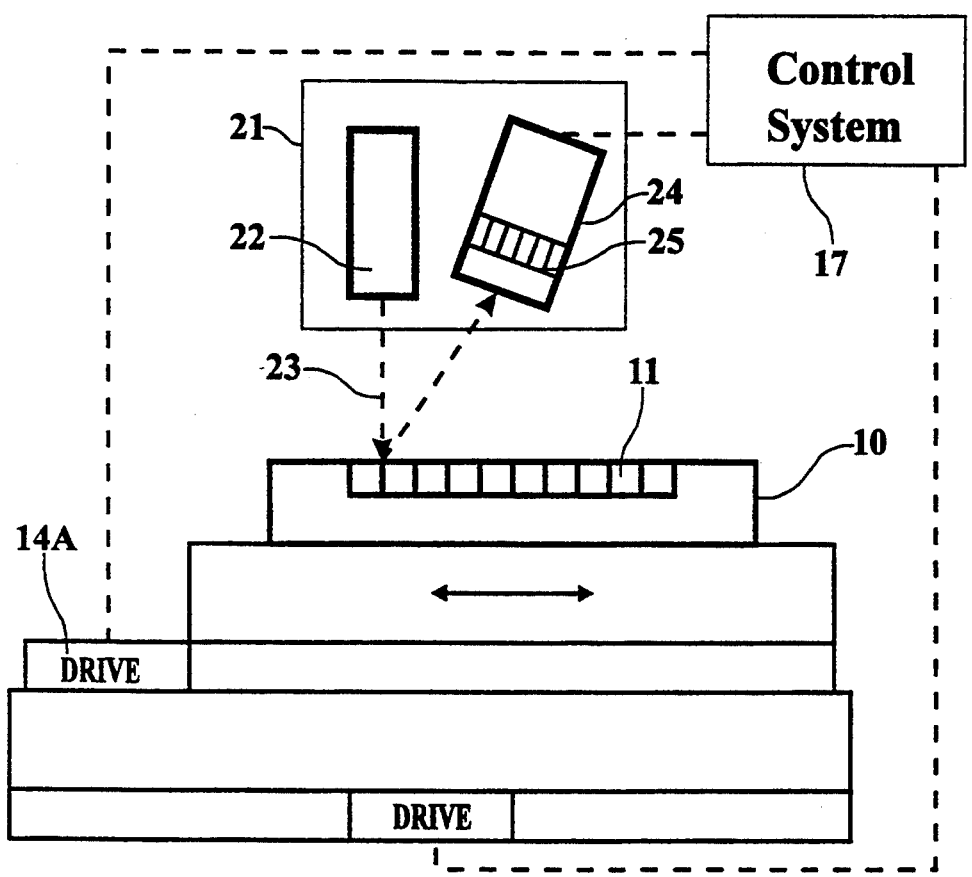
FIG. 1 is a schematic illustration of the modeling system of the present invention, taken in side elevational view.
Figure 2:
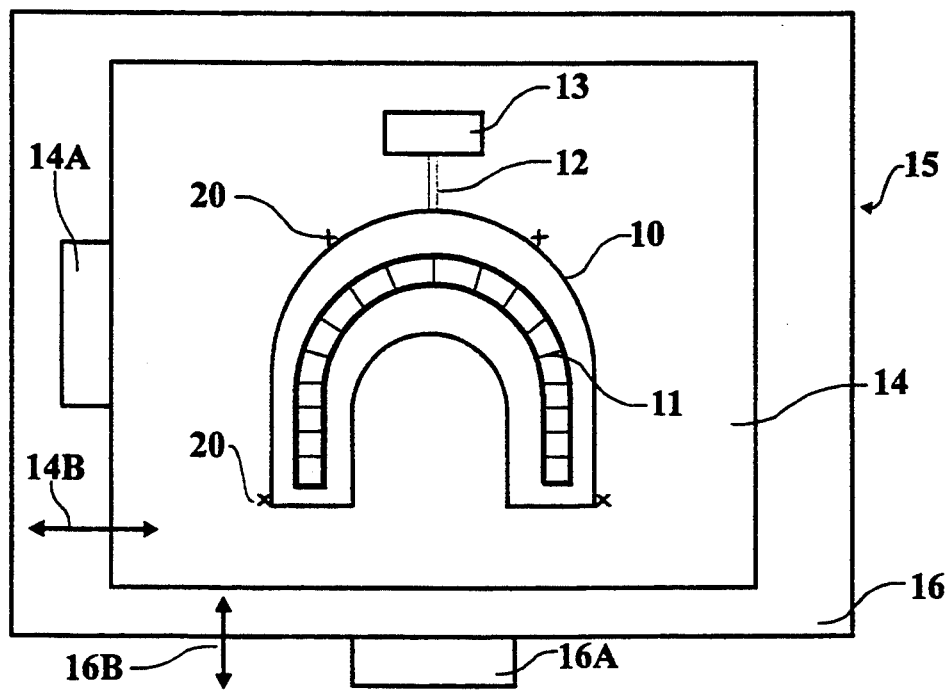
FIG. 2 is a similar schematic illustration taken in plan view.

In FIGS. 1 and 2 a conventional dental arch impression tray is indicated at 10 with the tray being filled by a conventional impression mold material in which the impression of the teeth is indicated at 11. The tray is mounted on a holder 12 carried in a pivot mount member 13. The pivot mount member 13 is carried on an X-table 14 of an X-Y table system generally indicated at 15 and including a Y-table 16. The X-table includes a drive system 14A allowing carefully controlled movement in an X direction 14B. The Y table includes a drive system 16A acting to drive the Y table in a controlled manner in the Y direction 16B. The X-way table system is driven from a central control unit 17 which acts as a data acquisition and X-Y-Z controlling computer system.

The impression of the dental arch is thus scanned by using the X-Y table under very accurate control from the control system. Thus the dental arch can be scanned by moving the Y table in discreet depth while scanning the X table back and forth within the bounds of the dental arch. In order to set up these bounds, the operator can initially set a number of datum points indicated at 20 by moving the X-Y table under manual control. This ensures that the scanning takes place only over the area of the dental arch.

During this scanning movement, the movement in one direction is effectively continuous so there is no need for stopping and starting of the table during the scanning action.

The measurement of the impression is effected in the Z direction by a laser range finding system schematically indicated at 21. This comprises a laser light source 22 which generates a beam 23 of laser light directed onto the impression in the Z direction that is at right angles to the X-Y plane. A detector 24 receives light scattered from the impact of the beam with the impression. The detector includes an area array of CCD detector elements 25 as described in more detail hereinafter. The detector elements provide information by way of a readout to the data acquisition and control system 17. In view of the continuous movement of the scanning action, the laser source is pulsed and the detection effected only during the very short pulse. As the pulse width (i.e. time span) is short and the table movement is slow, the amount of movement of the table during the pulse is very small and thus does not affect the accuracy of the detection, within reasonable bounds. For example, for a table movement speed of 25 mm/sec. which is a relative high speed for a precision X-Y table, and a pulse width 0.05 msec. which is a relative long pulse for the system, the table moves 1.25 μm only during the pulse. The typical table movement speed is 15 mm/sec and the pulse width is 0.02 msec.

The present system requires conventional dental arch impressions taken in stock or customized trays. Following conventional antiseptic procedures, the impressions are the inserted into the 12 shown schematically in FIG. 1. The digitization process is subsequently automated, requiring key-board or mouse instructions to control, modify or change the resultant three-dimensional simulation on the computer terminal. Both hard and software components are compatible with a PC-486 computer, and provision has been made for future additional input from digital radiographs and periodontal probes, in addition to other electronic patient records.

The coordinate measuring subsystem has a measurement volume of $100 \times 100 \times 25$ mm. This volume is designed to embrace dental arch impressions from adults and children, although provision has been made to accommodate more limited dental impressions. The measuring subsystem comprises an X-Y table with $100 \times 100$ mm travel, whereas Z-axis measurements are derived from the laser range measuring probe mounted on a stationary platform independent from the X-Y table. The laser range measuring probe has continuous movement and position readout capability of 25 mm, although provision has been made to modify this capability to the range of 10–40 mm. The measurement region and positioning of the laser range measuring probe on the Z-axis are adjusted automatically based on feedback from the dental impression video image. Thus the operator is required to position a targeting device on 4 to 6 points delineating the boundaries of the impression, prior to initiating the automated digitization process. Simple key-board instructions may also be required to change the specifications of the laser range measuring probe e.g. the dynamic measurement range, the measurement accuracy and the standoff, depending on the required precision of the subsequent simulation.

Since the dental impression is mounted in a standardized location on the X-Y table, the contained surface coordinates are automatically obtained from the X-Y table position indicator and the laser range data. The data acquisition rate is greatly increased by the application of customized 'measure by fly' techniques and the automatic adjustment of the X-Y table traveling speed during the continuous scanning action. This can be modulated by the operator, depending on the measurement accuracy required. The response time of the laser range measuring probe can be modified by key-board controls, in addition to tilting the X-Y table to facilitate measurement of 'obstructed' areas.

The resultant 3D data can then be stored in a computer disk, or transferred directly to a graphics software package for subsequent translation into a 3D simulation to be viewed on a computer terminal either in the dental office or some other central location.

The measured 3D dental impression coordinates are converted to simulated three-dimensional models of the maxillary or mandibular dental arches using a commercial solid modeling software package such as Auto CAD (Product of Autodesk, Inc.), but a customized solid modeling graphic software package is preferred because of unique user requirements. Such models can be viewed from any perspective or magnification by simple key-board or mouse controls, and any aspect can be printed on an office printer to facilitate appraisal by the dentist or patient. The software also allows for subsequent customized model segmentation: this facilitates the simulation of any component tooth movement determined by operator input, including extraction.

Software has also been developed whereby the maxillary and mandibular arch models can be aligned by key-board instructions so that centric relation coincides with centric occlusion. At this relationship, the points of maxillary and mandibular tooth contact can be identified with a color-code if required. There is again the potential for record keeping for future reference if required.

Further software modifications permit maxillary and mandibular arch simulations to be positioned in centric, protrusive and lateral excursive locations. This entails the use of the DMS to digitize the superior and inferior surfaces of conventional wax, polysulfone or silicone bite registrations from these three positions taken in situ. The maxillary and mandibular arch simulations can then be positioned into their respective locations on the digitized bite registration through key-board control.

Other software adaptations facilitate the following:
 i. The translation from static to dynamic dental arch simulations. This facility enables an operator to change the location or orientation of any tooth in the simulation, and then to move any or all other teeth independently to simulate potential treatment options for a particular patient. This facility has the potential to be included in an 'expert system'.
 ii. The three-dimensional simulation derived from one impression can be subtracted from an analogous simulation derived from a subsequent impression of the same patient through simple key-board inputs. This facility enables the effects of treatment progress or relapse on a patient to be objectively delineated.
 iii. By simple key-board or mouse controls, various occlusal adjustments and/or dental restorations can be included in the 3D simulations, to facilitate potential treatment option evaluations and their communication to patients.
 iv. Various options for inclusion of data derived from potential future sources have been provided for this software, i.e. the software is both versatile and user friendly. Operator manipulation options include a computer pointing device such as mouse, window icon, voice control etc., whereas the display terminal is controlled by an appropriate personnel computer such as PC-486 or equivalent.

Since the laser spot beam is generally conical in shape (circular or elliptical) with a Gaussian intensity distribution, the spot beam image will also be approximately conical shaped. When a CCD area array is used as an imaging detector, the image center can be determined more accurately by using prior knowledge of the image shape instead of the signal peak intensity position.

The detector used is an area CCD array of 512×32 elements. The amplitude of each CCD element is stored at the appropriate memory using a frame grabble. The signal from the center column CCD array is processed by a voltage comparator, so that an approximate image center position is obtained. Using the approximate position as the data array center, a rectangular array, say 41×31, is selected, assuming that the whole spot beam image is within the selected rectangular array. The rectangular array size depends on the spot beam image size and shape.

Since the laser beam spot intensity is a Gaussian distribution function, the image will have similar distribution function, except that the amplitude at each CCD cell is proportional to the total illumination on the cell. Three different threshold levels or predetermined levels of light intensity are used to process the image and lead to three concentric images of similar shape. Each image edge is then fitted to the theoretical shape and the image center of the fitted image obtained. The resultant image center is then the average of three fitted image centers.

A special circuit board incorporating the digital signal processing chips is constructed to process the image. The laser probe using this board can measure more than 1000 points per second.

A unique, economical and fast data acquisition rate optical arrangement has therefore been designed for any dental application by using a specially designed laser range probe and a small and accurate X-Y table.

The tilt mechanism 13 is actuated after an initial scanning action to tilt the dental arch about the axis of the holder 12 which raises one side of the arch relative to the opposed side vertically away from the X-Y plane. After tilting through a predetermined distance, the scanning action is repeated following which the tilt mechanism 13 is actuated to move the dental arch to a further tilted position generally opposed to the second tilted position. A third scanning action is then completed. These three scanning actions can then be compared and the data correlated to provide a more accurate calculation of the shape of the impression. In addition the tilting action can expose areas of the impression which are obscured by overhang. The potential applications of the present system can then be summarized in point form:
 (i). Laser scan digitization of dental arch form from dental impressions precludes the need for conventional study models.
 (ii). More precise arch form and tooth orientation appraisals are facilitated by digitized dental impressions compared with traditional study casts. The component maxillary and mandibular teeth can be viewed from any perspective and/or magnification, and any dimensions can be determined from point location of the simulation.
 (iii). Subtraction of digitized sequential dental impressions facilitates evaluations of treatment progress: this opens the potential for the institution of prompt remedial treatment.
 (iv). The capability of modifying the three-dimensional dental arch simulations interactively facilitates prior evaluations of potential treatment options and their presentation to patients.
 (v). Electronic dental models can be readily stored on computer disk, thereby facilitating filing and retrieval in addition to facilitating their communication to third parties.
 (vi). An interactive modeling capabilities potentiate the development of expert diagnostic and evaluative systems for dentistry.
 (vii). The specific advantages of this technology can only be cursorily summarized:
   (a). Orthodontics The effects of extracting specific teeth and realignment of the remainder of the arch can be readily simulated on the computer. In addition to aiding patient communication, this capability facilitates the specific orthodontic appliance design.

Subtraction or overlay of digitized sequential impressions not only provides objective appraisals of orthodontic treatment progress, (i.e., comparison with original simulation of final arch form) but also the prompt detection of abnormalities for their remedial treatment.

(b). Occlusal rehabilitation

Viewing dental arch simulations from any perspective or magnification facilitates delineation of premature cuspal interferences. The interactive modeling capability also enables the effects of cuspal modulation to be verified prior to in vivo transfer.

(c). Restorative dental treatment

Veneers or other complex restorations can be planned on the three-dimensional simulations prior to commencement. In addition, success of final treatment can then be verified by subtraction of the digitized final impression from the original simulation.

(d). Prosthodontic treatment

Fixed or removable prosthodontic appliances can be designed and evaluated on the three dimensional simulation prior to construction. This capability will facilitate the delivery of cost-effective prosthodontic treatment.

(e). Pedodontic treatment

Pedodontic treatment largely involves preservation of the deciduous dentition to permit the orderly eruption of the permanent teeth. In this regard, digitization of sequential impressions will not only facilitate the early detection or premature drifting and/or rotation but also the prompt institution of remedial therapy.

(f). Periodontal treatment

The ability to measure tooth movement from sequential impressions facilitates the detection of differential tooth drifting and rotation that complicates advanced periodontal destruction.

Figure 3:
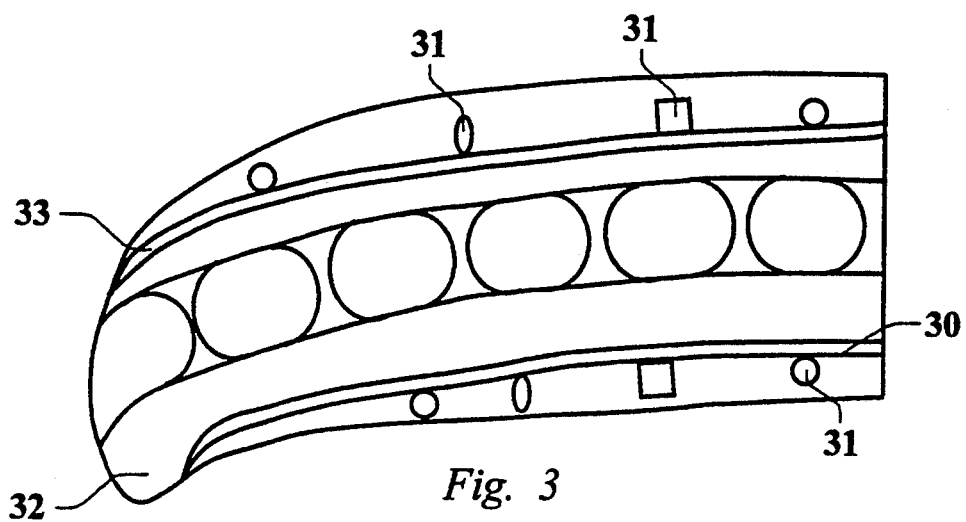
FIG. 3 is a top plan view of an alignment tray for taking alignment impressions of the mandibular and maxillar teeth of the patient.
Figure 4:
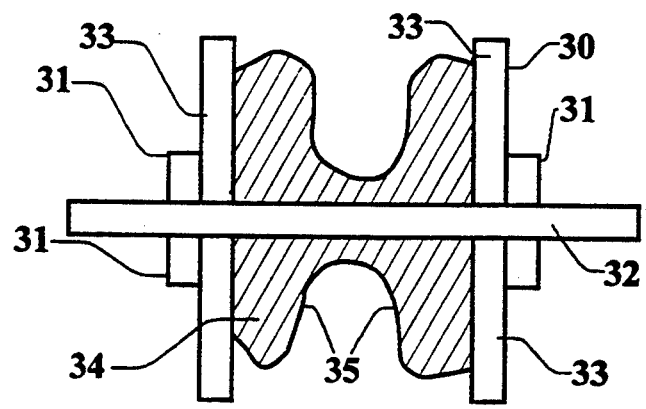
FIG. 4 is across-sectional view along the lines 4—4 of FIG. 3.

Dental study casts are traditionally aligned by using wax or other bite registrations in addition to partially integrated maxillary and mandibular dental impressions. Whereas existing clinical techniques are difficult to adapt for dental CAD systems, two modified techniques have been devised for the present system where the prime objective is precision. Turning therefore to FIGS. 3 and 4, there is shown an alignment impression tray 30 with predefined identification marks 31 at upper and lower sides.

The alignment tray comprises disposable non-transparent plastic or appropriate metal with an "H" shaped cross section. The horizontal partition wall 32 of the "H" channel is extended slightly at the outside of the vertical walls 33 and the thickness of the extension is known. Appropriate circular (or square or other simple shapes) cylindrical identification marks are positioned on the extension as shown in FIG. 2. The size, the height and the relative horizontal positions of each mark are known. The tray thus provides upper and lower containers for the mold material 34 into which the impression 35 is made by the patient biting into the material. This acts to generate a partial impression of both the mandibular and maxillar teeth of the patient. By measuring the partial maxillary dental impression with respect to the observable marks and the partial mandibular dental impression with respect to other set of observable marks, the relative positions between partial maxillary and mandibular dental impressions can be established. The teeth used in the partial dental impression are identified, and this information is used to compare with the full impressions previously taken so that the maxillary and mandibular dental arch can be aligned from the partial impression data. this has the advantage that the measurement setup for the alignment maxillary dental impression and the alignment mandibular dental impression is independent. It has the disadvantage that the alignment dental impression tray production cost will be high.

Figure 5:
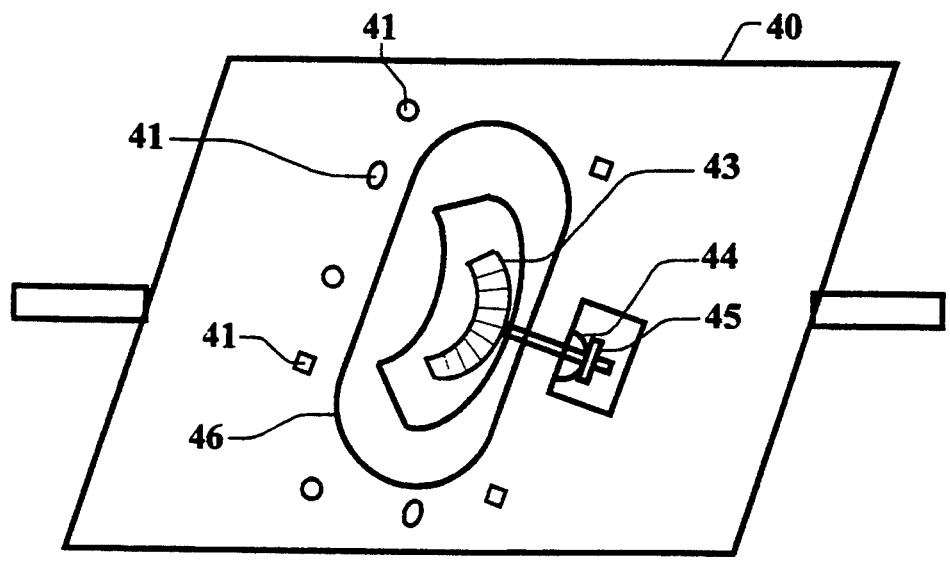
FIG. 5 is a schematic plan view of a holding jig for an alignment tray.

In a second arrangement shown in FIG. 5, a partial dental impression holding jig 40 is provided with predefined identification marks 41 at upper and lower sides.

Since the partial impression 43 is mounted on a measuring jig 40 both the partial mandibular impression and the partial maxillary impression can be measured by rotating the holding jig approximately 180 degree with respect to the horizontal axis. The identification marks are positioned on the holding jig 40 rotating platform surfaces since the partial dental impression does not move with respect to the platform surface during the measurement. The impression 43 is mounted in an opening 46 within the platform and is held in place by a spring 44 and a clamping nut 45. The use of the jig avoids the necessity for special alignment trays.

Since various modifications can be made in our invention as herein above described, and many apparently widely different embodiments of same made within the spirit and scope of the claims without departing from such spirit and scope, it is intended that all matter contained in the accompanying specification shall be interpreted as illustrative only and not in a limiting sense.

We claim:

1. A method of generating for manipulation a three-dimensional model, suitable for display and dimensional calculaton of teeth and dental arch of a patient comprising taking a molded impression of the teeth, placing the impression on a support table defining an X-Y plane, directing a beam of laser light onto the impression at a point of impact, relatively translating the beam of light and the impression in the X-Y plane so as to scan the impression with the beam to provide a plurality of points of impact each having a predetermined location in the X-Y plane, determining the distances of the points of impact of the beam with the impression in the Z direction by detecting a pattern of light reflected from the point, and generating the digital image by correlating the locations and the distances.

2. The method according to claim 1 wherein the relative movement is effected continuously and wherein the beam is pulsed, the pattern being detected for a respective location during the each pulse of the beam.

3. The method according to claim 1 wherein the beam is directed along a fixed first line transverse to the X-Y plane onto the impression so as to be confined to a limited region of the impression at the point of impact and wherein the impression is moved relative to the line.

4. The method according to claim 3 wherein the distance of each point is determined by providing an area array of detector elements at a predetermined position spaced from the region along a second line at an angle to the first line, the area array being arranged at a predetermined distance from the X-Y plane, and detecting on the area array light scattered by the region of the impression from the beam.

5. The method according to claim 4 including calculating from a pattern of the scattered light detected on the area array a theoretical center of the pattern and determining the position of the center on the array.

6. The method according to claim 5 wherein the center is calculated by determining a locus of predetermined light intensity less than a maximum value and by calculating a theoretical center of the locus.

7. The method according to claim 6 wherein a second theoretical center is calculated using a second predetermined light intensity and is compared to said theoretical center.

8. The method according to claim 1 including tilting the impression relative to the X-Y plane about an axis lying in the X-Y plane and repeating the steps of relatively translating the beam of light and the impression in the X-Y plane so as to scan the impression with the beam to provide a plurality of points of impact each having a predetermined location in the X-Y plane, determining the distances of the points of impact of the beam with the impression in the Z direction by detecting a pattern of light reflected from the point, and generating data relating to the three-dimensional model by correlating the locations and the distances.

9. The method according to claim 8 including tilting the impression a second time and correlating the data from three separate scans of the impression to generate said three-dimensional model.

10. The method according to claim 1 including defining in the X-Y plane a plurality of datum points relative to a dental arch shape of the impression and limiting the movement in the X-Y plane to scan substantially only the dental arch shape.

11. The method according to claim 1 including locating a light source and detector array in fixed position in a Z direction.

12. The method according to claim 1 including taking maxillary and mandibular dental impressions of the teeth of the patient, generating a digital image of each of the mandibular and maxillary impressions, taking a partial impression containing teeth from both the mandibular and maxillary teeth of the patient, generating a three-dimensional model of the teeth of the partial impression in association with a plurality of datum points located relative to both the teeth of the mandibular and maxillary teeth, and comparing the three-dimensional model of the partial impression with the three-dimensional models of the mandibular and maxillary impressions to locate the datum points relative to the three-dimensional models of the mandibular and maxillary impressions to determine the relative locations of the teeth in a bite (occlusal) position of the patient of the three-dimensional models of the mandibular and maxillary impressions.

13. The method according to claim 12 wherein the datum points are located on a dental tray carrying the impression.

14. The method according to claim 12 wherein the datum points are located on a support plate and wherein the impression is carried on the support plate, the impression being rotatable through an angle of the order of 180 degrees to locate the datum points firstly relative to the mandibular teeth and secondly relative to the maxillary teeth.

15. The method according to claim 12 including manipulating the three-dimensional models of the mandibular and maxillary teeth in conjunction with the datum points so as to simulate jaw movement from an open position of the teeth to the bite (occlusal) position of the teeth.

* * * * *